(12) United States Patent
Mabrouk

(10) Patent No.: US 8,318,806 B2
(45) Date of Patent: Nov. 27, 2012

(54) DEODORIZING COMPOSITION AND METHOD OF FORMING THEREOF

(75) Inventor: Issa Mabrouk, Grafton, OH (US)

(73) Assignee: Zorbx Inc., Strongsville, OH (US)

( * ) Notice: Subject to any disclaimer, the term of this patent is extended or adjusted under 35 U.S.C. 154(b) by 504 days.

(21) Appl. No.: 12/245,062

(22) Filed: Oct. 3, 2008

(65) Prior Publication Data

US 2009/0092568 A1  Apr. 9, 2009

Related U.S. Application Data

(60) Provisional application No. 60/977,244, filed on Oct. 3, 2007.

(51) Int. Cl.
- *A61Q 15/00* (2006.01)
- *A61K 8/27* (2006.01)
- *A61K 8/365* (2006.01)
- *A61L 101/36* (2006.01)
- *A61L 9/01* (2006.01)
- *A01N 37/00* (2006.01)
- *A61K 31/201* (2006.01)

(52) U.S. Cl. .......................... 514/560; 424/67

(58) Field of Classification Search ................ None
See application file for complete search history.

(56) References Cited

U.S. PATENT DOCUMENTS

| | | | |
|---|---|---|---|
| 3,697,453 A * | 10/1972 | Tate et al. ............... 510/480 |
| 5,593,670 A | 1/1997 | Trinh et al. |
| 5,780,020 A | 7/1998 | Peterson et al. |
| 5,861,143 A | 1/1999 | Peterson et al. |
| 5,861,144 A | 1/1999 | Peterson et al. |
| 5,885,599 A | 3/1999 | Peterson et al. |
| 6,004,584 A | 12/1999 | Peterson et al. |
| 6,451,749 B1 * | 9/2002 | Murphy et al. ............... 510/287 |
| 6,495,058 B1 * | 12/2002 | Frankenbach et al. ....... 252/8.91 |
| 6,528,047 B2 | 3/2003 | Arif et al. |
| 7,226,584 B2 | 6/2007 | Lersch et al. |
| 2002/0009424 A1 | 1/2002 | Kandathil et al. |
| 2003/0007945 A1 | 1/2003 | Arif et al. |
| 2003/0026820 A1 * | 2/2003 | De Lacharriere et al. ..... 424/401 |
| 2003/0053970 A1 * | 3/2003 | Bruening et al. ............... 424/66 |
| 2003/0133892 A1 | 7/2003 | Lersch et al. |
| 2003/0161798 A1 * | 8/2003 | Kellner et al. ............... 424/64 |
| 2003/0235550 A1 * | 12/2003 | Pan et al. ............... 424/70.16 |
| 2004/0234466 A1 * | 11/2004 | Banowski et al. ............... 424/65 |
| 2006/0045860 A1 | 3/2006 | Gupta |
| 2006/0222621 A1 | 10/2006 | Kuhn et al. |
| 2007/0049511 A1 | 3/2007 | Lawshe et al. |
| 2007/0154427 A1 | 7/2007 | Lersch et al. |

FOREIGN PATENT DOCUMENTS

| | | |
|---|---|---|
| DE | 37 26 636 | 10/1988 |
| DE | 38 08 114 | 9/1989 |
| DE | 40 14 055 | 4/1993 |
| WO | WO 96/05358 | 2/1996 |
| WO | WO 98/18439 | 5/1998 |
| WO | WO 98/56340 | 12/1998 |
| WO | WO 99/44566 | 9/1999 |
| WO | WO 00/35413 | 6/2000 |
| WO | WO 2006/105680 | 10/2006 |

OTHER PUBLICATIONS (definition: friable Oxford English Dictionary 1989).*
"Material Safety Data Sheet", Degussa, TEGO SORB PY 88 T.Q., Nov. 13, 2004.
"Material Safety Data Sheet", Lanxess, Baypure CX 100/34%, Jul. 2, 2004.

* cited by examiner

*Primary Examiner* — James H. Alstrum-Acevedo
*Assistant Examiner* — Jessica Kassa
(74) *Attorney, Agent, or Firm* — Fay Sharpe LLP

(57) ABSTRACT

An odor absorbing composition is provided comprising zinc salt of ricinoleic acid, a solubility promoter including sodium iminodisuccinate, water and optionally, other ingredients such as perfumes and antifungal agents or bactericides. The zinc ricinoleate can be completely solubilized in water, yet the solution will exhibit low foaming and friability. In addition, the end product may be in the form of a sprayable liquid, a thick liquid capable of clinging to a vertical surface, a gel or solid tablet, a powder, or any other form. The present invention further relates to a method for forming an odor absorbing composition comprising zinc salt of ricinoleate acid, sodium iminodisuccinate and water.

15 Claims, No Drawings

DEODORIZING COMPOSITION AND METHOD OF FORMING THEREOF

BACKGROUND

The present invention relates to preparations with deodorizing action, and more particularly to deodorizing preparations which comprise the zinc salt of ricinoleic acid and at least one amino-functional amino acid, salt and/or derivative thereof. However, it is to be appreciated that the present exemplary embodiment is also amenable to other like applications.

BACKGROUND OF THE INVENTION

The formation of perspiration is a normal and healthy bodily function. Perspiration, in itself, is odorless. However, the degradation of the protein compounds present in perspiration by natural, Gram-positive skin bacteria produces body odor, which in today's society is typically perceived as overpowering, repulsive and neglectful. For this reason, a large number of cosmetic products have been developed for body care with the aim of eliminating this unpleasant odor of perspiration. Application forms of such products, which include both odor-inhibiting deodorants and also perspiration-inhibiting antiperspirants, comprise sticks, creams, soaps, roll-ons, as well as aerosols and pump sprays.

Likewise, there is a great need for other deodorizing compositions suitable for use in a wide range of applications. Air, carpet, and upholstery deodorizers are in high demand, especially for those individuals who live with pets, who smoke, or for environments with a potential for strong odors. A large number of commercial products are available for this market segment as well.

There are various active principles which are useful in these standard commercial formulations. For example, some deodorants conceal the unpleasant odors through the addition of perfumes. Usually, deodorants also comprise antimicrobial active ingredients such as Triclosan®, ethereal oils or Farnesol®. Such materials act as bactericides or bacteriostats to reduce the natural bacterial flora on the skin or other surfaces, thus preventing the formation of odor. Likewise prior art deodorant products also include enzyme blockers, such as triethyl citrate, which intervene in the enzymatic mechanism of bacterial decomposition of perspiration by preventing the formation of unpleasant-smelling degradation products by deactivating the ester-cleaving lipases. For personal deodorants, a further possibility is the use of antiperspirants, which reduce the perspiration secretion. The active ingredients used are aluminum and zirconium salts which, due to their protein-precipitating nature, narrow the sweat glands and thus reduce the formation of perspiration. Furthermore, so-called odor absorbers are also known. Odor absorbers are substances which can chemically or physically bond the odor-forming compounds by adsorption or absorption, respectively. One representative of such odor absorber material is zinc salts of ricinoleic acid.

The patent literature also includes descriptions in which these zinc salts are used in combinations with zinc salts of abietic acid or with zinc salts of other saturated or unsaturated hydroxylated fatty acids having 16 or more carbon atoms, and other active ingredients listed above.

Zinc ricinoleate can chemically bond to odor-intensive organic substances with sulfur or nitrogen containing functional groups, including, for example, mercaptans, thioethers, low molecular weight carboxylic acids, such as isovaleric acid, as well as amines. A particular advantage of this type of odor removal is that the bacterial equilibrium of the skin flora is not adversely affected as a result.

The ability of zinc ricinoleate to chemically bond to substances of this type and negate their odor causing potential permits zinc ricinoleate to be used in industrial areas of application for reducing unpleasant domestic and industrial odors.

However, due to its polymeric salt structure, zinc ricinoleate can only be used directly to a limited degree. Zinc ricinoleate is a compound which is only sparingly soluble in customary solvents, including water. In order to obtain effective preparations, zinc ricinoleate must be used in combination with solvents, surfactants, and solubility promoters. The typical solvents used are mono-or polyhydric alcohols, optionally with the addition of water. Customarily used highly ethoxylated solubility promoters are unable, even in high concentrations, to keep the zinc ricinoleate in solution by themselves and flowable products are also not obtained as a result.

Examples of special solubility promoters for zinc ricinoleate can be found in the patent literature. For example, German Patent Application DE-B-37 26 636 describes deodorants based on zinc ricinoleate with solvents and solubility promoters, where the solubility promoters used are the hydrolyzed ene adducts of ricinic fatty acids and maleic anhydride.

German Patent Application DE-B-38 08 114 likewise describes deodorants based on zinc ricinoleate with solvent and solubility promoters. The solubility promoters used in this prior art reference are partial esters of di- or polyhydroxy-alkanes, mono- and disaccharides, polyethylene glycols or alkanolamines with the ene adducts of maleic anhydride formed onto at least monounsaturated carboxylic acids with a chain length of from 10 to 25 carbon atoms and acid numbers from 10 to 140, which are preferably buffered to pH values around 6.5 with amino and/or amido compounds, such as triethanolamine, or glycol esters of aspartic acid and of glutamic acid as a result of the formation of salt-like bonds.

Preparations with these solubility promoters, however, are not flowable and the deodorant solutions formulated therefrom tend toward clouding and precipitation of individual components even at very low water levels.

One improvement is the solution proposed in the German Patent Application DE-B-40 14 055, in which the applicants describe compositions with deodorizing action, comprising the zinc salt of ricinoleic acid and/or the zinc salt of abetic acid and/or further zinc salts of other saturated or unsaturated hydroxylated fatty acids having 16 or more carbon atoms, and also 5 to 50%, by weight, of an ethoxylated fatty alcohol with straight or branched alkyl chain and a carbon number between 10 and 18 with fewer than 30 ethylene oxide units per molecule, and 5 to 30%, by weight, of a tertiary amine. The tertiary amines disclosed in the '055 reference are tertiary amino alcohols, such as, for example, triethanolamine or N,N,N',N'-tetrakis(2-hydroxypropyl)ethylenediamine.

The amino alcohols present in the prior art do not represent any problem for technical applications where there is no skin contact. For use in applications with skin contact, such as, in cosmetic products, however, more and more alternatives to amino alcohols are desired since the amino alcohols often comprise impurities of secondary amines. In addition, amino alcohols have also received negative reports due to sensitizing and allergic reactions upon their use on skin.

Accordingly, there is still a need for further improvement. For instance, the solubility in water or dilutability with water of the formulations without additional mono-and polyhydric alcohols as solubility promoters has still not been satisfactorily achieved. In addition, such formulations generally do not exhibit two important properties that are sought after in many applications: low foaming and friability.

SUMMARY OF THE INVENTION

The present invention provides preparations with deodorizing action, comprising a) the zinc salt of ricinoleic acid; b) sodium iminodisuccinate; c) water; and d) optionally, other ingredients such as perfumes and antifungal agents or bactericides. The present formulations provide a form of zinc ricinoleate that can be completely solubilized in water, yet the solution will exhibit low foaming and friability. In addition, the end product can be in the form of a sprayable liquid, a thick liquid capable of clinging to a vertical surface, a gel or solid tablet, a powder, or any other form.

These additional utilities are also of interest for the application area of domestic and industrial odors, since such systems are primarily aqueous, some of them also being further diluted. Through the choice of the auxiliaries used it is simultaneously possible to achieve better ecological compatibility of the deodorizing system.

The present invention further provides for a method for forming an odor absorbing preparation. Zinc salt of ricinoleic acid is mixed into an aqueous solution of sodium iminodisuccinate and water until the zinc salt of ricinoleic acid is completely dissolved.

Finally, the present invention provides for uses of these preparations in deodorizing hygienic and cosmetic formulations, deodorizing household cleaners, industrial cleaners, adsorbents in filters, deodorizing formulations for use in private and commercial animal keeping, deodorizing formulations for the treatment of textile fibers and fabrics.

DETAILED DESCRIPTION OF THE INVENTION

As stated above, the present invention provides preparations with deodorizing action which include the zinc salt of ricinoleic acid, sodium iminodisuccinate and water. The inventive preparations may further include other additives as optional components.

The zinc salts of ricinoleic acid suitable for use in the present invention may be obtained commercially from various manufacturers under their respective trade names, such as, e.g., TEGO® Sorb PY 88 TQ from Goldschmidt Chemical Corporation in Hopewell, Va.

In one embodiment, the zinc salt of ricinoleic acid (zinc ricinoleate) can be used in an amount of from about 0.1 to 60% by weight, preferably in an amount of from 2 to 20%, by weight, based on the total weight of the composition.

The solubilizer for the zinc ricinoleate includes sodium iminodisuccinate. Aqueous solutions of sodium iminodisuccinate are available commercially from various manufacturers under various trade names. An exemplary composition is a 34% aqueous solution of sodium iminodisuccinate available from Bayer under the trade name BAYPURE CX. In one embodiment, the sodium iminodisuccinate can be used in amounts of from about 1 to about 30% by weight, preferably in an amount of from 2 to 10% by weight, based on the total weight of the composition.

Although no additional solubilizing agent is necessary, one or more additional solubility promoters may be included in the composition if desired. Suitable solubility promoters include: nonionic and ionic surfactants, such as alkoxylates, polyglycerols, glycol ethers, glycols, polyethylene glycols, polypropylene glycols, polybutylene glycols, glycerol ester ethoxylates, polysorbates, alkyl ether sulfates, alkyl- and/or arylsulfonates, alkyl sulfates, ester sulfonates (sulfo-fatty acid esters), ligninsulfonates, fatty acid cyanamides, anionic sulfosuccinic acid surfactants, fatty acid isethionates, acylaminoalkane-sulfonates (fatty acid taurides), fatty acid sarcosinates, ether carboxylic acids and alkyl(ether)phosphates.

Suitable nonionic solubility promoters include $C_2$-$C_6$-alkylene glycols and poly-$C_2$-$C_3$-alkylene glycol ethers, optionally, etherified on one side with a $C_1$-$C_6$-alkanol and having, on average, 1 to 9 identical or different, preferably identical, alkylene glycol groups per molecule, and also alcohols and fatty alcohol polyglycol ethers, preferably propylene glycol, dipropylene glycol, trimethylolpropane, and fatty alcohols with low degrees of ethoxylation having 6 to 22, preferably 8 to 18, more preferably 8 to 12, and even more preferably 8 to 11, carbon atoms.

Suitable ionic solubility promoters are alkyl ether sulfates, sulfosuccinic acid surfactants, polyacrylates and phosphonic acids, preferably lauryl sulfate, lauryl ether sulfate, sodium sulfosuccinic acid diisooctyl ester, 1-hydroxyethane-1,1-diphosphonic acid, and diacetyltartaric esters.

These solubility promoters can be co-used in amounts of from 0 to 20% by weight, based on the total weight of the composition.

The water used may be deionized, filtered, demineralized, or alternatively tap water, preferably tap water with degrees of hardness which is sufficiently low so as not to impede the effectiveness of the composition.

Other components may also be added to the formulation. For example, the additional use of alcohols in particular ethanol, or isopropyl alcohol, is possible and is not excluded since such additives can be used for aesthetic and preservative purposes, in amounts and circumstances where skin irritation is not an issue.

Additionally, one or more additional odor control agents may be used. These may include zeolites, carbon odor-controlling agents, sodium bicarbonates, antimicrobial agents and/or antiperspirant ingredients for added body odor control. The antimicrobial agents of the present invention are selected from a group consisting of antibacterial agents, antifungal agents, and mixtures thereof. Antimicrobial agents help destroy and/or control the amount of bacteria and/or fungi present on the skin. Preferred antimicrobial agents are zinc phenolsulfonate, zinc oxide, zinc chloride, triclosan, Zelec® AM by DuPont, zinc undecylenate, and mixtures thereof. More preferred are zinc phenolsulfonate, zinc oxide, and triclosan. Triclosan is available from Ciba-Geigy as Irgasan DP-300.

One or more perfume agents may also be added to the composition if desired. Non-limiting examples of suitable volatile perfume ingredients which can be used in the compositions of this invention are amyl benzoate, beta-caryophyllene, cinnamic alcohol, diphenyl methane, dodecalactone, ethyl methyl phenyl glycidate, eugenol, fenchyl acetate, gamma-n-methyl ionone, heliotropine, indole, isobutyl quinoline, Lilial (p-t-Bucinal), methyl-N-methyl anthranilate, para-methoxy acetophenone, phenethyl butyrate, phenyl heptanol, phenyl hexanol, and phenoxy ethyl proprionate.

The compositions of the present invention also optionally include skin aids. The term "skin aids", as used herein, refers to skin protectants, emollients, and moisturizers. Preferred emollients and moisturizers are tocopherol, tocopheryl acetate, aloe, vegetable oils, mineral oil, petrolatum, jojoba oil, and mixtures thereof.

When used on the underarms, antiperspirant ingredients may be included.

Other optional additives include slip agents, binders, antipruritic agents, and colorants. These optional additives used in the present invention are products which are known in the respective field of use, and can be used in customary amounts.

The compositions can be prepared by mixing the components in any customary manner, such as, for example, by simultaneous, portionwise or successive addition of zinc ricinoleate to an initial charge of stirred and, optionally, heated aqueous sodium iminodisuccinate solution, and the subsequent metered addition of the further optionally included components.

The active ingredient combinations can be incorporated into all customary deodorant formulations. These include: pump spray solutions, liquid soaps, deodorant sprays and deodorant creams. It is also possible to add the corresponding formulations to other customarily used cosmetic products, such as, for example, hair shampoos or hair rinses, provided known incompatibilities do not exclude this from the outset. Another potential is to formulate a non-aqueous composition using the zinc ricinoleate and sodium iminodisuccinate in an anhydrous tablet or one incorporating only a minute amount of water. The tablet could then be added to a water based solution or otherwise rehydrated for subsequent use.

These active ingredient combinations can also be used in cleaning formulations, such as, for example, in hand dishwashing detergents, all-purpose cleaners, carpet cleaners, deowipes or as air freshener, deodorizing household cleaners, industrial cleaners, adsorbents in filters, deodorizing formulations for use in domestic and commercial animal keeping, deodorizing formulations for the treatment of textile fibers and fabrics.

By using the inventive active ingredient combinations, it is possible to prepare stable, deodorant formulations which do not precipitate out in aqueous solutions.

The deodorants according to the present invention, their preparation and use are illustrated in more detail in the example below. The chemical characterization of the trade names mentioned in the example are given above.

| Components | Amount (% by weight) |
|---|---|
| Part A | |
| BAYPURE CX | 12.0 |
| Water | 20.0 |
| Sodium citrate | 2.0 |
| Tego Sorb PY 88 TQ | 4.0 |
| Part B | |
| Water | 60.0 |
| Part C | |
| Isopropyl alcohol | 2.0 |

Components of part A were mixed at a temperature of 90° C. until the Tego Sorb was completely dissolved. Part B was then added slowly to part A. The mixture was cooled to 30° C. and part C was added with continued mixing until solution is clear.

The exemplary embodiment has been described with reference to the preferred embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

What is claimed is:

1. An odor absorbing composition consisting of from 0.1 wt % to about 60 wt % of an odor absorbing zinc salt of ricinoleic acid completely solubilized in: from about 1 wt % to 30 wt % sodium iminodisuccinate; sodium citrate; optionally one or more ingredients selected from the group consisting of solubility promoter(s), odor control agent(s), perfume agent(s), skin aid(s); and the balance water, based on the total weight of the composition.

2. The composition of claim 1, wherein said zinc salt of ricinoleic acid comprises 4.0 wt % of said composition.

3. The composition of claim 1, wherein said sodium iminodisuccinate comprises about 12.0 wt % of said composition.

4. The composition of claim 1, wherein said solubility promoter(s) is/are selected from the group consisting of ionic and nonionic surfactants, polyglycerols, glycol ethers, glycols, polyethylene glycols, polypropylene, glycols, polybutylene glycols, glycerol ester ethoxylates, polysorbates, alkyl ether sulfates, alkylsulfonates, arylsulfonates, alkyl sulfates, ester sulfonates, ligninsulfonates, fatty acid cyanamides, anionic sulfosuccinic acid surfactants, fatty acid isethionates, acylaminoalkane-sulfonates, fatty acid sarcosinates, ether carboxylic acids and alkyl (ether)phosphates.

5. The composition of claim 4, wherein each solubility promoter comprises 1 to 20 wt. % of the total composition.

6. The composition of claim 4, wherein said ionic surfactants are at least one of alkyl ether sulfates, sulfosuccinic acid surfactants, polyacrylates, phosphonic acids, lauryl sulfate, lauryl ether sulfate, sodium sulfosuccinic acid diisooctyl ester, 1-hydroxyethane-1,1-diphosphonic acid, and diacetyltartaric esters.

7. The composition of claim 4, wherein said nonionic surfactants are at least one of $C_2$-$C_6$-alkylene glycols, poly-$C_2$-$C_3$-alkylene glycol ethers, alcohols, fatty alcohol polyglycol ethers, and fatty alcohols with a low degree ethoxylation.

8. The composition of claim 1, wherein the water is one of deionized, filtered, demineralized, and tap water.

9. The composition of claim 1, wherein said odor control agent(s) is/are selected from the group consisting of zeolites, carbon odor-controlling agents, sodium bicarbonates, antimicrobial agents and/or antiperspirant ingredients.

10. The composition of claim 9, wherein said antimicrobial agents are at least one of consisted of antibacterial agents, antifungal agents, and mixtures thereof.

11. The composition of claim 1, wherein said perfume agent(s) is/are selected from the group consisting of amyl benzoate, beta-caryophyllene, cinnamic alcohol, diphenyl methane, dodecalactone, ethyl methyl phenyl glycidate, eugenol, fenchyl acetate, gamma-n-methyl ionone, heliotropine, indole, isobutyl quinoline, Lilial (p-t-Bucinal), methyl-N-methyl anthranilate, para-methoxy acetophenone, phenethyl butyrate, phenyl heptanol, phenyl hexanol, and phenoxy ethyl proprionate.

12. The composition of claim 1, wherein said skin aid(s) is/are selected from the group consisting of skin protectants, emollients, and moisturizers.

13. The composition of claim 1, wherein said composition is incorporated into at least one of a pump spray solution, liquid soap, deodorant sprays, deodorants creams, shampoos and cleaning formulations.

14. A method for forming an odor absorbing composition in accord with the composition of claim 1, the method comprising:

mixing zinc said salt of ricinoleic acid into an aqueous solution of sodium iminodisuccinate, sodium citrate, and water until said zinc salt of ricinoleic acid is dissolved; and proportionally adding said one or more optional ingredients.

15. The method of claim 14, wherein said mixing step comprises the portionwise addition of zinc rinoleate to a heated solution of sodium iminodisuccinate and sodium citrate.

* * * * *